(12) United States Patent
Higashiyama et al.

(10) Patent No.: US 6,645,963 B2
(45) Date of Patent: Nov. 11, 2003

(54) PROLONGED-ACTION EYE DROP

(75) Inventors: Masayo Higashiyama, Kobe (JP);
Akira Ohtori, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 14 days.

(21) Appl. No.: 09/802,849

(22) Filed: Mar. 12, 2001

(65) Prior Publication Data

US 2001/0012859 A1 Aug. 9, 2001

Related U.S. Application Data

(62) Division of application No. 09/509,258, filed as application No. PCT/JP98/04965 on Nov. 2, 1998, now abandoned.

(30) Foreign Application Priority Data

Nov. 5, 1997 (JP) .............................................. 9-302802
Sep. 3, 1998 (JP) ........................................... 10-250009

(51) Int. Cl.[7] ............................................ A61K 31/535
(52) U.S. Cl. .................... 514/235.8; 514/557; 514/558; 514/912
(58) Field of Search ......................... 514/235.8, 231.5, 514/912, 557, 558

(56) References Cited

U.S. PATENT DOCUMENTS 5,434,187 A   7/1995   Egerer et al. ................ 514/574
5,554,367 A   9/1996   Ali et al. .................. 424/78.04
5,767,143 A   6/1998   Lehmussaari et al. ...... 514/397
5,883,108 A * 3/1999   DeSantis, Jr. ............... 514/317

FOREIGN PATENT DOCUMENTS

EP     0 590 786      4/1994
JP     63-301822     12/1988
JP     2563336        9/1996

OTHER PUBLICATIONS

M. R. Gasco et al., "Microemulsions as topical delivery vehicles: ocular administration of timolol", Journal of Pharmaceutical & Biomedical Analysis, vol. 7, No. 4, pp. 433–439, 1989.

H. Sasaki et al., "Ophthalmic preservatives as absorption promoters for ocular drug delivery", J. Pharm. Pharmacol., vol. 47, No. 47, pp. 703–707, 1995.

H. Sasaki et al., "Different effects of absorption promoters on corneal and conjunctval penetration of ophthalmic Beta–blockers", Pharmaceutical Research, vol. 12, No. 8, pp. 1146–1150, 1995.

* cited by examiner

Primary Examiner—Zohreh Fay
(74) Attorney, Agent, or Firm—Wenderoth, Lind & Ponack, L.L.P.

(57) ABSTRACT

Eye drops containing a β-blocker such as cartelol hydrochloride are improved in the penetration of the β-blocker into the eye and the retention thereof in the eye tissues by the incorporation of a $C_{3-7}$ fatty acid such as sorbic acid to the eye preparations.

4 Claims, 4 Drawing Sheets

PROLONGED-ACTION EYE DROP

This application is a divisional of Ser. No. 09/509,258 filed Mar. 24, 2000 now abandoned, which is a 371 of PCT/JP98/04965 filed Nov. 2, 1998.

TECHNICAL FIELD

The present invention relates to an eye drop comprising a β-blocker and a $C_3$–$C_7$ fatty acid or the salt thereof. Also, the present invention relates to a method to promote penetration of a β-blocker into the eye and to improve the retention of the β-blocker in the ocular tissues by incorporating a $C_3$–$C_7$ fatty acid or the salt thereof into an eye drop containing the β-blocker.

BACKGROUND OF THE INVENTION

Recently, the β-blockers, such as carteolol hydrochloride, timolol maleate, betaxolol hydrochloride and the like, are used as a medicine for glaucoma in the form of the eye drop. However, many of the active components of the eye drops such as carteolol hydrochloride have high water-solubility, and in these cases, the highly hydrophobic corneal epithelium becomes a barrier to the penetration of the components into the eye. It is therefore necessary to instill the eye drop containing the components in high dose or many times in order to get the sufficient amount of the components penetrated in the eye tissues for lowering an intraocular pressure. However, in order to separate from the systemic effect of the β-blocker, to get more effect on lowering intraocular pressure and to get the prolonged-action of the β-blocker, it is preferable to promote penetration of the drugs into the eye and to prolong retention of the drug in the eye than to instill a high dose of the eye drop and to instill many times.

From the above view point, it has been investigated to improve the permeability of the β-blocker into cornea, and it is reported that capric acid ($C_{10}$ saturated fatty acid) promotes the permeability of the β-blocker such as atenolol, carteolol, tilisolol and timolol into cornea in vitro (H. Sasaki et al., Pharm. Research. 12(8), 1146–1150 (1995)) and that the instillation of the eye drop containing ion pair of caprylic acid ($C_8$ saturated fatty acid) and timolol to a rabbit increases the amount of timolol penetrated into aqueous humor (M. R. Gasco et al., J. Pharm. Biomed. Anal. 7, 433–439 (1989)). JP Patent No. 2563336 also discloses that bunazosin hydrochloride of a sympathetic a $α_1$ receptor blocker can enhance the permeability into cornea by incorporating caproic acid, caprylic acid and capric acid ($C_6$–$C_{10}$ linear fatty acids)

However, in the prior art, it can not be found any data or any description showing that the retention time of the β-blocker or the sympathetic a $α_1$ receptor blocker in the ocular tissues is prolonged, but only the descriptions of the promotion of the drug penetration into cornea and the increase of the amount of the drug permeated in aqueous humor.

On the other hand, sorbic acid of $C_6$ unsaturated fatty acid is a compound commonly used as a preservative of agents for a contact lens because of its becteriostatic effect. However, there is no report showing that the unsaturated fatty acid such as sorbic acid accelerates the penetration of the drugs into the eye by the instillation of the eye drop, but on the contrary, there has been reported that the acid has no effect on the corneal permeability of tilisolol of the β-blocker in vitro (J. Pharm. Pharmacol. 47, 703–707 (1995)). There is also no prior art concerning the effect of the $C_3$–$C_7$ fatty acids on the corneal permeability of the β-blocker.

DISCLOSURE OF THE INVENTION

The object of the present invention is to provide an dye drop capable of promoting the penetration of a β-blocker such as carteolol hydrochloride, timolol maleate and betaxolol hydrochloride, and to improve the retention of the drug in the ocular tissues.

Herein, the penetration into the eye means that the drug after the instillation permeates into corneal epithelium and the like and penetrates into the ocular tissues such as corneal stroma, aqueous humor, iris and ciliary body, lens, vitreous body and retina.

As the results of the extensive studies by the present inventors, it was found that the sorbic acid which does not show any action promoting the permeation of the β-blocker into cornea in vitro promotes the amount of penetration of the β-blocker in vivo and prolongs the retention period of β-blocker in the ocular tissues. Furthermore, it was also found that the $C_3$–$C_7$ fatty acid accelerates the penetration of β-blocker into the eye, thence the present invention was accomplished.

Namely, the present invention relates to
(1) an eye drop comprising a β-blocker and a $C_3$–$C_7$ fatty acid or the salt thereof,
(2) the eye drop according to (1), wherein the β-blocker is carteolol or the salt thereof,
(3) the eye drop according to (1), wherein the β-blocker is timolol or the salt thereof,
(4) the eye drop according to (1), wherein the β-blocker is betaxolol or the salt thereof,
(5) the eye drop according to one of (1) to (4), wherein the $C_3$–$C_7$ fatty acid is an unsaturated fatty acid,
(6) the eye drop according to one of (1) to (5), wherein the $C_3$–$C_7$ fatty acid is a $C_6$ unsaturated fatty acid,
(7) the eye drop according to (6), wherein the $C_6$ unsaturated fatty acid is sorbic acid,
(8) a method for promoting the penetration of a β-blocker into the eye and improving the retention of the β-blocker in the ocular tissues which comprises incorporating a $C_3$–$C_7$ fatty acid or the salt thereof into an eye drop containing the β-blocker.

As the β-blocker used for the eye drop of the present invention, for example, carteolol, timolol, betaxolol, befunolol, metipranolol, levobunolol and the like which are used as a medicine for glaucoma may be used. Among them, carteolol, timolol and betaxolol may be used preferably.

As the pharmaceutically acceptable salt of the β-blocker used for the eye drop of the present invention, there are exemplified by acid addition salts such as hydrochloride, sulfate, nitrate, hydrobromide, hydroiodide, phosphate, acetate, maleate, fumarate, citrate and tartrate. Among the above salts, hydrochloride and maleate are preferable.

The concentration of the β-blocker or the salt thereof (hereinafter, may be simply called as "the β-blocker") used for the eye drop of the present invention is different depending on the degree of glaucoma, but may be usually about 0.02 to 3 w/v %, preferably about 0.05 to 2 w/v %, more preferably about 0.1 to 2 w/v %.

The $C_3$–$C_7$ fatty acid (hereinafter, may be simply called as "the fatty acid"), preferably the $C_4$–$C_6$ fatty acid may be used for the eye drop of the present invention. The fatty acid used in the present invention may be one of a straight or a branched and a saturated or an unsaturated monocarboxylic acid and dicarboxylic acid, preferably propionic acid, butyric acid, isobutyric acid, valeric acid, pivalic acid, caproic acid, heptanoic acid, malonic acid, succinic acid, glutaric acid, adipic acid, pimelic acid, crotonic acid, sorbic acid, maleic acid, fumaric acid and the like, more preferably sorbic acid. As the salt of the fatty acid, there are exemplified by sodium salt, potassium salt and the like.

The concentration of the fatty acid or the salt thereof used for the eye drop of the present invention is different depending on the kind of β-blocker, but may be usually about 0.01 to 10 w/v %, preferably about 0.02 to 5 w/v %, more preferably about 0.04 to 2 w/v %. In the ratio of the fatty acid or the salt thereof to the β-blocker, the fatty acid or the salt thereof may be usually 0.01 to 10 weight ratio, preferably 0.05 to 3 weight ratio, more preferably 0.1 to 5 weight ratio, relative to 1 weight of the β-blocker. Also, the ratio of the fatty acid or the salt thereof may be 0.2 to 5 moles, preferably 0.2 to 2 moles, relative to 1 mole of carteolol hydrochloride, may be 0.2 to 10 moles, preferably 1 to 5 moles, relative to 1 mole of timolol maleate, and may be 0.5 to 10 moles, preferably 2 to 5 moles, relative to 1 mole of betaxolol hydrochloride.

pH of the eye drop of the present invention may be adjusted usually to 4.5 to 8.5, preferably 5 to 8, more preferably 6 to 7.

To the eye drop of the present invention, additives usually used for the eye drop, for example, isotonic agents (sodium chloride, potassium chloride, glycerin, mannitol, sorbitol, boric acid, glucose and propylene glycol, etc.), buffer (phosphate buffer, acetate buffer, borate buffer, carbonate buffer, citrate buffer, tris buffer, glutamic acid and ε-aminocaproic acid, etc.), preservatives (benzalkonium chloride, benzethonium chloride, chlorhexidine gluconate, chlorobutanol, benzyl alcohol, sodium dehydroacetate, parahydroxybenzoates, sodium edetate and boric acid, etc.), stabilizers (sodium bisulfite, sodium thiosulfate, sodium edetate, sodium citrate, ascorbic acid and dibutylhydroxytoluene, etc.), thickening agents (water-soluble cellulose derivatives such as methylcellulose, hydroxyethylcellulose, hydroxypropylmethylcellulose and carboxymethylcellulose; sodium chondroitin sulfate, sodium hyaluronate, carboxyvinylpolymer, polyvinyl alcohol, polyvinylpyrrolidone and macrogol, etc.), pH adjusters such as hydrochloric acid, sodium hydroxide, phosphoric acid and acetic acid may be added, if desired. The amount of the additives is different depending on the kind of the additives and the purpose thereof, but may be a concentration capable of accomplishing the purpose thereof. The isotonic agents may be usually added in an amount to give 0.8 to 1.2 of the osmotic pressure ratio. The buffers may be added in an amount of about 0.01 to 2 w/v %. The stabilizers may be added in an amount of about 0.001 to 1 w/v %. And the thickening agents may be added in an amount of about 0.001 to 3 w/v %.

To the eye drop of the present invention, other pharmaceutical components other than the β-blocker may be appropriately added not so far as the object of the present invention is deviated.

The eye drop of the present invention may be produced according to the usual method for producing the eye drop, for example, a method described in Ophthalmic Solutions of General Rules for Preparations (JP, 13th edition).

Because the eye drop of the present invention promotes the penetration of the β-blocker into the eye and improves the retention of the β-blocker in the ocular tissues, the frequency of the instillation can be decreased and the bother in instilling many times can be avoided. The sufficient effect is obtained also when the incorporated amount of the drug is decreased. Concretely, for example, in case that the eye drop containing carteolol hydrochloride 1 w/v % is used for the adult patient suffering from glaucoma, it may be instilled once about 1 drop per 1 to 3 days, preferably once about 1 drop per 1 day. In case that timolol maleate 0.68 w/v % (0.5 w/v % as timolol) is employed, the eye drop may be instilled once about 1 drop per 1 day.

BEST MODE FOR CARRYING OUT THE INVENTION

The present invention is further explained by the following Test Examples and Examples, but not limited thereto.

EXAMPLE 1

Eye Drop

According to the usual method, a carteolol hydrochloride eye drop comprising the following components was prepared.

| | |
|---|---|
| Carteolol hydrochloride | 2.0 g |
| Sorbic acid | 0.3 g |
| Sodium dihydrogen phosphate | 0.1 g |
| Sodium chloride | 0.7 g |
| Benzalkonium chloride | 0.005 g |
| Sodium hydroxide | q.s. |
| Sterilized pure water | total 100 ml |
| pH | 7.0 |

EXAMPLE 2

According to the usual method, a carteolol hydrochloride eye drop comprising the following components was prepared.

| | |
|---|---|
| Carteolol hydrochloride | 2.0 g |
| Sorbic acid | 0.3 g |
| Sodium dihydrogen phosphate | 0.1 g |
| Sodium chloride | 0.43 g |
| Benzalkonium chloride | 0.005 g |
| Sodium hydroxide | q.s. |
| Sterilized pure water | total 100 ml |
| pH | 7.0 |

EXAMPLE 3

According to the usual method, a carteolol hydrochloride eye drop comprising the following components was prepared.

| | |
|---|---|
| Carteolol hydrochloride | 1.0 g |
| Sorbic acid | 0.3 g |
| Sodium dihydrogen phosphate | 0.1 g |
| Sodium chloride | 0.53 g |
| Benzalkonium chloride | 0.005 g |
| Sodium hydroxide | q.s. |
| Sterilized pure water | total 100 ml |
| pH | 6.5 |

EXAMPLE 4

According to the usual method, a carteolol hydrochloride eye drop comprising the following components was prepared.

| | |
|---|---|
| Carteolol hydrochloride | 2.0 g |
| Sorbic acid | 0.15 g |
| Sodium dihydrogen phosphate | 0.1 g |
| Sodium chloride | 0.47 g |
| Benzalkonium chloride | 0.005 g |
| Sodium hydroxide | q.s. |
| Sterilized pure water | total 100 ml |
| pH | 6.5 |

EXAMPLE 5

According to the usual method, a carteolol hydrochloride eye drop comprising the following components was prepared.

| | |
|---|---|
| Carteolol hydrochloride | 2.0 g |
| Sorbic acid | 0.51 g |
| Sodium dihydrogen phosphate | 0.1 g |
| Sodium chloride | 0.29 g |
| Benzalkonium chloride | 0.005 g |
| Sodium hydroxide | q.s. |
| Sterilized pure water | total 100 ml |
| pH | 7.0 |

EXAMPLE 6

According to the usual method, a carteolol hydrochloride eye drop comprising the following components was prepared.

| | |
|---|---|
| Carteolol hydrochloride | 0.5 g |
| Sorbic acid | 0.17 g |
| Sodium dihydrogen phosphate | 0.1 g |
| Sodium chloride | 0.16 g |
| Benzalkonium chloride | 0.005 g |
| Sodium hydroxide | q.s. |
| Sterilized pure water | total 100 ml |
| pH | 7.0 |

EXAMPLE 7

According to the usual method, a carteolol hydrochloride eye drop comprising the following components was prepared.

| | |
|---|---|
| Carteolol hydrochloride | 2.0 g |
| Sorbic acid | 1.36 g |
| Sodium dihydrogen phosphate | 0.1 g |
| Benzalkonium chloride | 0.005 g |
| Sodium hydroxide | q.s. |
| Sterilized pure water | total 100 ml |
| pH | 7.0 |

EXAMPLE 8

According to the usual method, a timolol maleate eye drop comprising the following components was prepared.

| | |
|---|---|
| Timolol maleate | 0.68 g |
| Sorbic acid | 0.35 g |
| Sodium dihydrogen phosphate | 0.1 g |
| Sodium chloride | 0.56 g |
| Benzalkonium chloride | 0.005 g |
| Sodium hydroxide | q.s. |
| Sterilized pure water | total 100 ml |
| pH | 7.0 |

EXAMPLE 9

According to the usual method, a timolol maleate eye drop comprising the following components was prepared.

| | |
|---|---|
| Timolol maleate | 0.68 g |
| Sorbic acid | 0.046 g |
| Sodium dihydrogen phosphate | 0.1 g |
| Sodium chloride | 0.7 g |
| Benzalkonium chloride | 0.005 g |
| Sodium hydroxide | q.s. |
| Sterilized pure water | total 100 ml |
| pH | 6.5 |

EXAMPLE 10

According to the usual method, a timolol maleate eye drop comprising the following components was prepared.

| | |
|---|---|
| Timolol maleate | 0.68 g |
| Sorbic acid | 0.18 g |
| Sodium dihydrogen phosphate | 0.1 g |
| Sodium chloride | 0.63 g |
| Benzalkonium chloride | 0.005 g |
| Sodium hydroxide | q.s. |
| Sterilized pure water | total 100 ml |
| pH | 6.5 |

EXAMPLE 11

According to the usual method, a timolol maleate eye drop comprising the following components was prepared.

| | |
|---|---|
| Timolol maleate | 0.34 g |
| Sorbic acid | 0.35 g |
| Sodium dihydrogen phosphate | 0.1 g |
| Sodium chloride | 0.37 g |
| Benzalkonium chloride | 0.005 g |
| Sodium hydroxide | q.s. |
| Sterilized pure water | total 100 ml |
| pH | 7.0 |

EXAMPLE 12

According to the usual method, a timolol maleate eye drop comprising the following components was prepared.

| | |
|---|---|
| Timolol maleate | 0.68 g |
| Sorbic acid | 1.76 g |
| Sodium dihydrogen phosphate | 0.1 g |
| Benzalkonium chloride | 0.005 g |
| Sodium hydroxide | q.s. |
| Sterilized pure water | total 100 ml |
| pH | 7.0 |

EXAMPLE 13

According to the usual method, a betaxolol hydrochloride eye drop comprising the following components was prepared.

| | |
|---|---|
| Betaxolol hydrochloride | 0.56 g |
| Sorbic acid | 0.91 g |
| Sodium dihydrogen phosphate | 0.1 g |
| Benzalkonium chloride | 0.005 g |
| Sodium hydroxide | q.s. |
| Sterilized pure water | total 100 ml |
| pH | 7.0 |

EXAMPLE 14

According to the usual method, a betaxolol hydrochloride eye drop comprising the following components was prepared.

| | |
|---|---|
| Betaxolol hydrochloride | 0.56 g |
| Sorbic acid | 0.37 g |
| Sodium dihydrogen phosphate | 0.1 g |
| Sodium chloride | 0.56 g |
| Benzalkonium chloride | 0.005 g |
| Sodium hydroxide | q.s. |

-continued

| | |
|---|---|
| Sterilized pure water | total 100 ml |
| pH | 7.0 |

EXAMPLE 15

According to the usual method, a betaxolol hydrochloride eye drop comprising the following components was prepared.

| | |
|---|---|
| Betaxolol hydrochloride | 0.56 g |
| Sorbic acid | 0.18 g |
| Sodium dihydrogen phosphate | 0.1 g |
| Sodium chloride | 0.65 g |
| Benzalkonium chloride | 0.005 g |
| Sodium hydroxide | q.s. |
| Sterilized pure water | total 100 ml |
| pH | 7.0 |

EXAMPLE 16

According to the usual method, a betaxolol hydrochloride eye drop comprising the following components was prepared.

| | |
|---|---|
| Betaxolol hydrochloride | 0.56 g |
| Sorbic acid | 0.09 g |
| Sodium dihydrogen phosphate | 0.1 g |
| Sodium chloride | 0.7 g |
| Benzalkonium chloride | 0.005 g |
| Sodium hydroxide | q.s. |
| Sterilized pure water | total 100 ml |
| pH | 7.0 |

EXAMPLE 17

According to the usual method, a carteolol hydrochloride eye drop comprising the following components was prepared.

| | |
|---|---|
| Carteolol hydrochloride | 2.0 g |
| Caproic acid | 0.31 g |
| Sodium dihydrogen phosphate | 0.1 g |
| Sodium chloride | 0.41 g |
| Benzalkonium chloride | 0.005 g |
| Sodium hydroxide | q.s. |
| Sterilized pure water | total 100 ml |
| pH | 7.0 |

EXAMPLE 18

According to the usual method, a carteolol hydrochloride eye drop comprising the following components was prepared.

| | |
|---|---|
| Carteolol hydrochloride | 2.0 g |
| Crotonic acid | 0.23 g |
| Sodium dihydrogen phosphate | 0.1 g |
| Sodium chloride | 0.41 g |

-continued

| | |
|---|---|
| Benzalkonium chloride | 0.005 g |
| Sodium hydroxide | q.s. |
| Sterilized pure water | total 100 ml |
| pH | 7.0 |

EXAMPLE 19

According to the usual method, a carteolol hydrochloride eye drop comprising the following components was prepared.

| | |
|---|---|
| Carteolol hydrochloride | 2.0 g |
| Butyric acid | 0.24 g |
| Sodium dihydrogen phosphate | 0.1 g |
| Sodium chloride | 0.4 g |
| Benzalkonium chloride | 0.005 g |
| Sodium hydroxide | q.s. |
| Sterilized pure water | total 100 ml |
| pH | 7.0 |

EXAMPLE 20

Eye Drop

According to the usual method, a carteolol hydrochloride eye drop comprising the following components was prepared.

| | |
|---|---|
| Carteolol hydrochloride | 2.0 g |
| Sorbic acid | 0.3 g |
| Sodium dihydrogen phosphate | 0.1 g |
| Sodium chloride | 0.7 g |
| Sodium hydroxide | q.s. |
| Sterilized pure water | total 100 ml |
| pH | 7.0 |

TEST EXAMPLE 1

Test of the Penetration of Carteolol Hydrochloride into Eye of Arbino Rabbit (Experimental Method)

50 μl of the eye drop of Example 1 was instilled once to the male arbino rabbit. The rabbit was slaughtered to withdraw the aqueous humor after 1 hour of the instillation, then the concentration of carteolol hydrochloride in aqueous humor was measured. As the control, an eye drop prepared by omitting sorbic acid from the components of Example 1 was instilled to the rabbit. In the same manner as above, the concentration of carteolol hydrochloride in aqueous humor was measured.

(Results of the Experiment)

Figure 1:
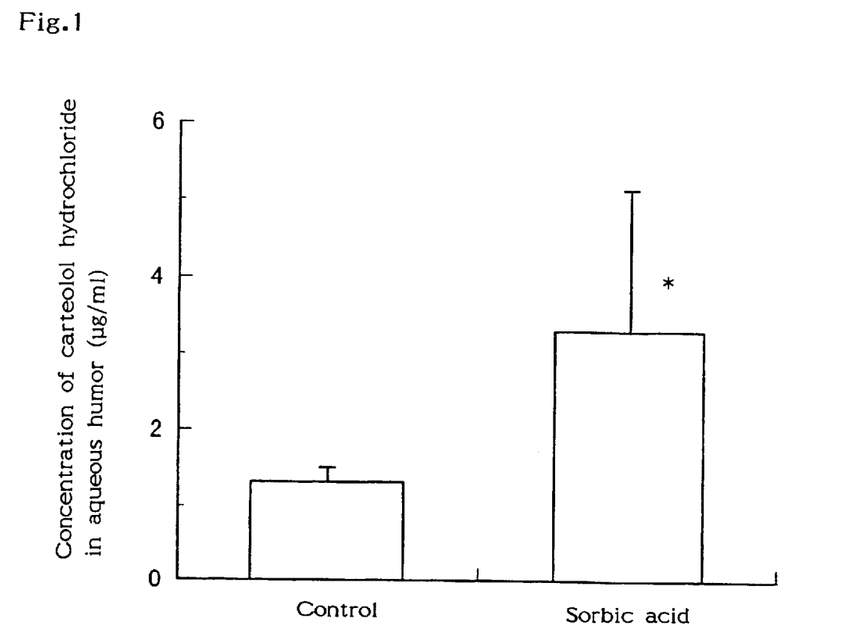
FIG. 1 is a graph showing the amount of carteolol hydrochloride in aqueous humor at the time of 1 hour after the instillation of the eye drop (containing 2 w/v % carteolol hydrochloride) of Example 1 in Test Example 1. The horizontal axis shows the test group and the vertical axis shows the concentration of carteolol hydrochloride in aqueous humor ($\mu$g/ml). Each value shows the mean value±standard deviation (4 samples). * shows the significance $p<0.05$ against the control group by the student-t test.

The results are shown in FIG. 1. The amount of carteolol hydrochloride in aqueous humor was 3 times higher for the eye drop containing sorbic acid than that of the eye drop without sorbic acid.

The above results show that the penetration of carteolol hydrochloride into the eye is promoted by incorporating sorbic acid in the eye drop containing carteolol hydrochloride.

TEST EXAMPLE 2

Test of the Retention of Carteolol Hydrochloride in the Ocular Tissues of the Pigmented Rabbit (Experimental Method)

50 µl of the eye drop of Example 20 was instilled once to the male pigmented Dutch rabbit. Each rabbit was slaughtered to withdraw the aqueous humor at post-instillation times of 0.5, 1, 2, 4, 6, 12 and 24 hours, then cornea and iris-ciliary body were excised to measure the concentration of carteolol hydrochloride in cornea, aqueous humor and iris-ciliary body. As the control, an eye drop prepared by omitting sorbic acid from the components of Example 20 was instilled to the rabbit. In the same manner as above, the concentration of carteolol hydrochloride in cornea, aqueous humor and iris-ciliary body was measured.

(Results of the Experiment)

Figure 2:
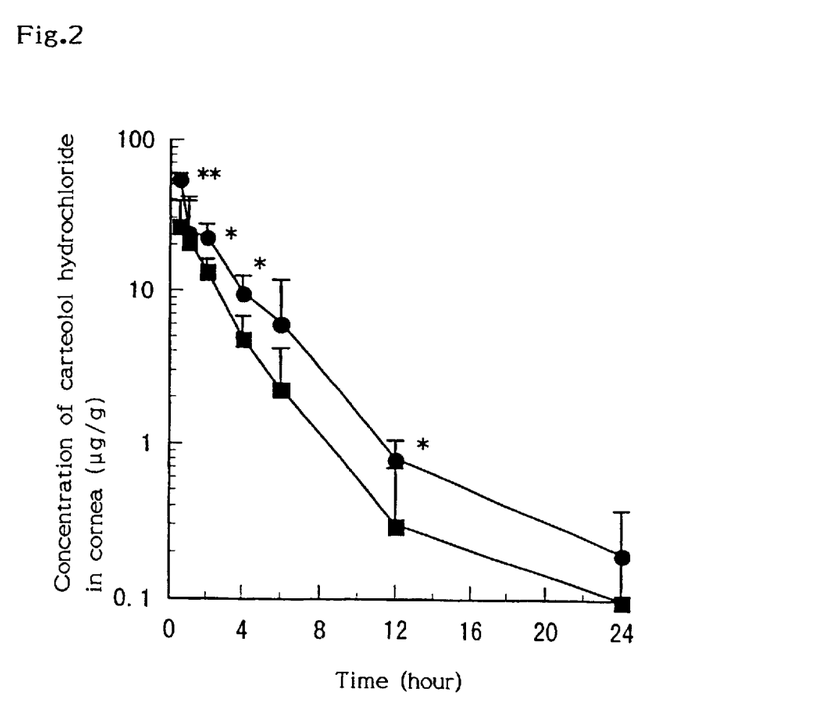
FIG. 2 is a graph showing the time course of concentration of carteolol hydrochloride in cornea after the instillation of the eye drop (containing 2 w/v % carteolol hydrochloride) of Example 20 in Test Example 2. The horizontal axis shows the time (hour) and the vertical axis shows the concentration of carteolol hydrochloride in cornea ($\mu$g/g). Each value shows the mean value±standard deviation (4 samples). The black circles show the case that the eye drop of Example 20 is instilled and the black squares show the case the eye drop prepared by omitting sorbic acid from the components in Example 20. ** shows the significance $p<0.01$ and * shows $p<0.05$, against the control group by the student-t test.

(1) The time course of concentration of carteolol hydrochloride in cornea is shown in FIG. 2. The eye drop containing sorbic acid gave the delay of elimination of carteolol hydrochloride from the cornea and the high concentration thereof at every time as compared with the eye drop without sorbic acid used as the control. The area under the curve (AUC) for drug concentration-time profiles in cornea was 1:9 time higher for the eye drop containing sorbic acid than that of the control.

Figure 3:
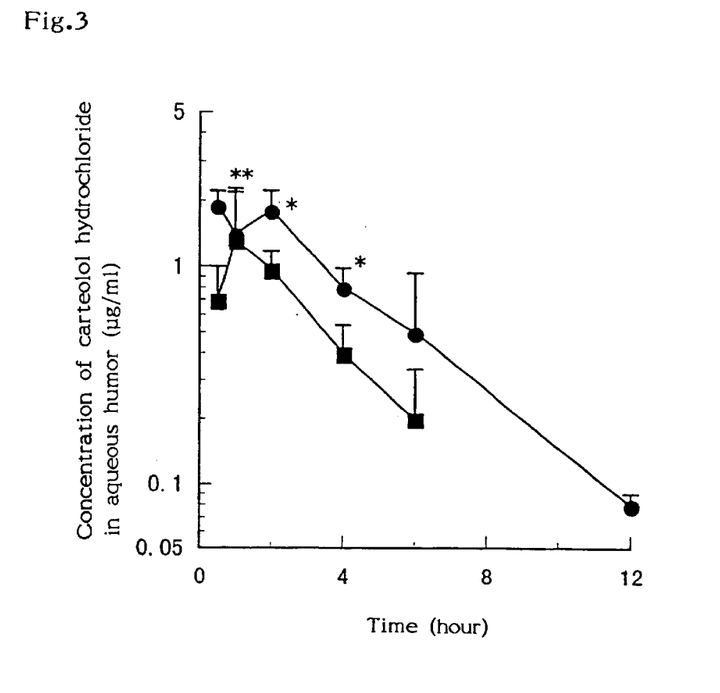
FIG. 3 is a graph showing the time course of concentration of carteolol hydrochloride in aqeos humor after the instillation of the eye drop (containing 2 w/v % carteolol hydrochloride) of Example 20 in Test Example 2. The horizontal axis shows the time (hour) and the vertical axis shows the concentration of carteolol hydrochloride in aqueous humor ($\mu$g/ml). Each value shows the mean value±standard deviation (4 samples). The black circles show the case that the eye drop of Example 20 is instilled and the black squares show the case the eye drop prepared by omitting sorbic acid from the components in Example 20. ** shows the significance $p<0.01$ and * shows $p<0.05$, against the control group by the student-t test.

(2) The time course of concentration of carteolol hydrochloride in aqueous humor is shown in FIG. 3. Similarly with the case of cornea, the eye drop containing sorbic acid gave the delay of elimination of carteolol hydrochloride in aqueous humor and the high concentration thereof at every time as compared with the eye drop without sorbic acid used as the control. The area under the curve for the drug concentration-time profiles in aqueous humor for the eye drop containing sorbic acid was about 2.1 times higher than that of the control.

Figure 4:
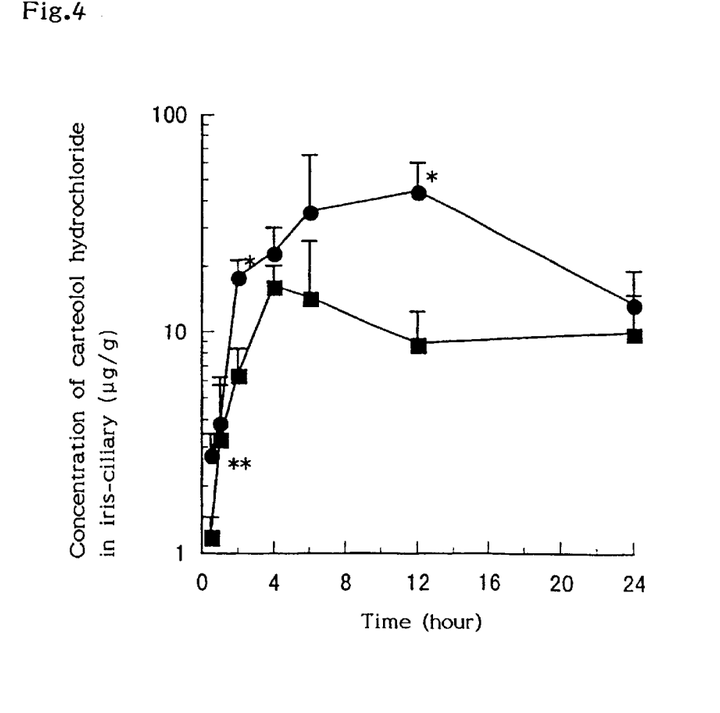
FIG. 4 is a graph showing the time course of concentration of carteolol hydrochloride in iris and ciliary body after the instillation of the eye drop (containing 2 w/v % cartelol hydrochloride) of Example 20 in Test Example 2. The horizontal axis shows the time (hour) and the vertical axis shows the concentration of carteolol hydrochloride in iris and ciliary body ($\mu$g/g). Each value shows the mean value±standard deviation (4 samples). The black circles show the case that the eye drop of Example 20 is instilled and the black squares show the case the eye drop prepared by omitting sorbic acid from the components in Example 20. ** shows the significance $p<0.01$ and * shows $p<0.05$, against the control group by the student-t test.

(3) The time course of the concentration of carteolol hydrochloride in iris-ciliary body is shown in FIG. 4. The eye drop containing sorbic acid gave high concentration of carteolol hydrochloride in the iris-ciliary body as compared with that of the eye drop without sorbic acid used as the control. The area under the curve for the drug concentration-time profiles in the iris-ciliary body for the eye drop containing sorbic acid was about 3.6 times higher than that of the control.

The above results show that the retention period of carteolol hydrochloride in the ocular tissues is improved because carteolol hydrochloride in the intraocular tissues is kept at the high concentration and because the elimination of carteolol hydrochloride in the ocular tissues is delayed by incorporating sorbic acid in the eye drop containing carteolol hydrochloride.

TEST EXAMPLE 3

Test of the Penetration of Timolol Maleate into the Eye of the Arbino Rabbit (Experimental Method)

50 µl of the eye drop of Example 8 was instilled once to the male arbino rabbit. Each rabbit was slaughtered to withdraw the aqueous humor at post-instillation of 15, 30 minutes, 1 and 3 hours, then cornea and iris-ciliary body were excised to measure the concentration of timolol maleate in aqueous humor, cornea and iris-ciliary body. As the control, 0.5% Timoptol® (produced by Banyu Pharmaceutical Co., Ltd.) was instilled to the rabbit. In the same manner as above, the concentration of timolol maleate in aqueous humor, cornea and iris-ciliary body was measured.

(Results of the Experiment)

Figure 5:
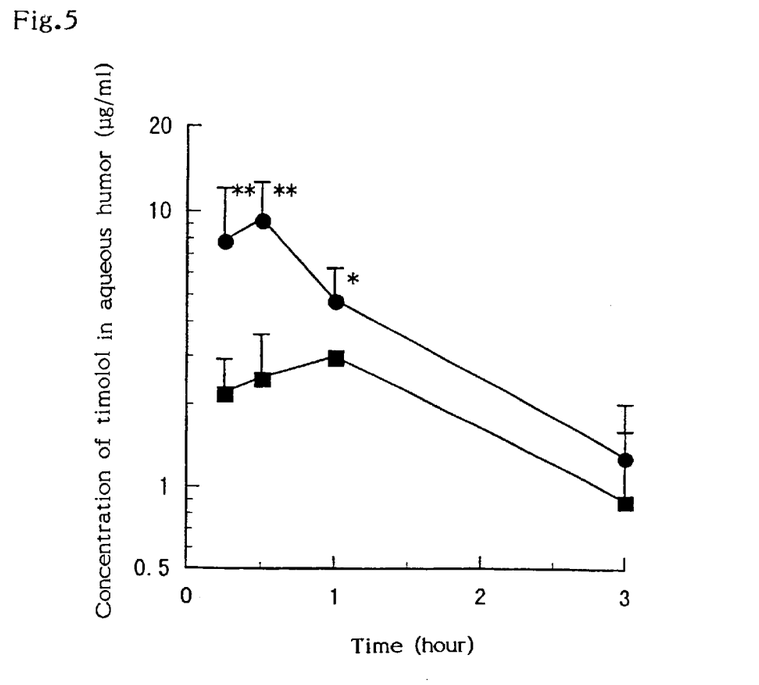
FIG. 5 is a graph showing the time course of concentration of timolol in aqueous humor after the instillation of the eye drop (containing 0.68 w/v % timolol maleate) of Example 8 in Test Example 3. The horizontal axis shows the time (hour) and the vertical axis shows the concentration of timolol in aqueous humor ($\mu$g/ml). Each value shows the mean value±standard deviation (5 samples). The black circles show the case that the eye drop of Example 8 is instilled and the black squares show the case the eye drop prepared by omitting sorbic acid from the components in Example 8. ** shows the significance $p<0.01$ and * shows $p<0.05$, against the control group by the student-t test.

(1) The concentration-time profiles of timolol in aqueous humor is shown in FIG. 5. The concentration of timolol in aqueous humor at each post-instillation time of 15 minutes and 30 minutes was about 3.6 times higher for the eye drop containing sorbic acid and about 3.8 times higher, respectively, than that of the control. Also, the concentration of timolol for the eye drop containing sorbic acid was higher at every time and the area under the curve (AUC) for the drug concentration-time profiles in aqueous humor was about 2.2 times higher than that of the control.

Figure 6:
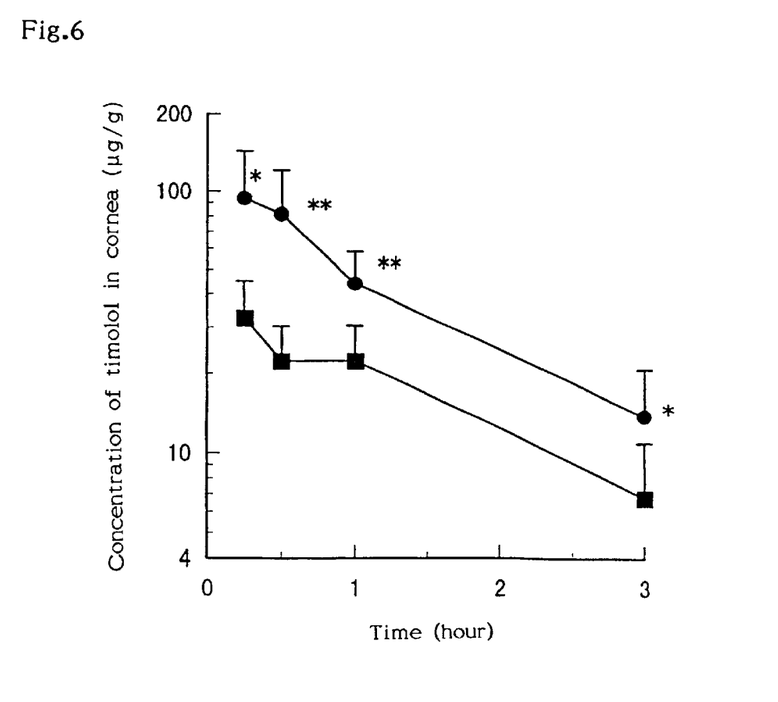
FIG. 6 is a graph showing the time course of concentration of timolol in cornea after the instillation of the eye drop (containing 0.68 w/v % timolol maleate) of Example 8 in Test Example 3. The horizontal axis shows the time (hour) and the vertical axis shows the concentration of timolol in cornea (pg/g). Each value shows the mean value±standard deviation (5 samples). The black circles show the case that the eye drop of Example 8 is instilled and the black squares show the case the eye drop prepared by omitting sorbic acid from the components in Example 8. ** shows the significance $p<0.01$ and * shows $p<0.05$, against the control group by the student-t test.

(2) The drug concentration-time profiles of timolol in cornea is shown in FIG. 6. The concentration of timolol in cornea at each post-instillation time of 15 minutes and 30 minutes was 2.9 times higher for the eye drop containing sorbic acid and about 3.6 times higher, respectively than that of the control. Also, similarly with the drug concentration in aqueous humor, the concentration of timolol in cornea for the eye drop containing sorbic acid was kept at higher concentration at every time and the area under the curve (AUC) for the drug concentration-time profiles in cornea was about 2.4 times higher than that of the control.

Figure 7:
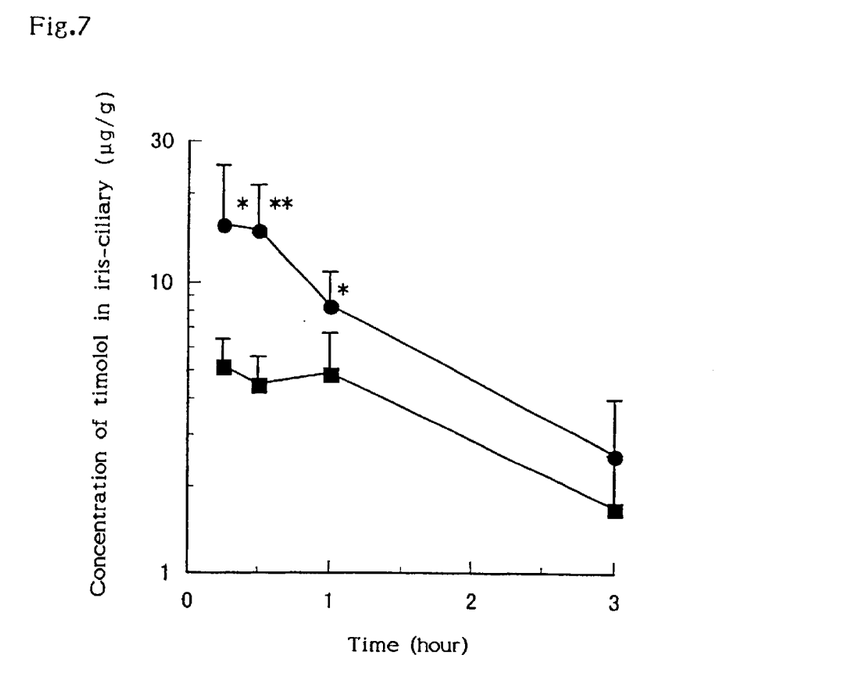
FIG. 7 is a graph showing the time course of concentraton of timolol in iris and ciliary body after the instillation of the eye drop (containing 0.68 w/v % timolol maleate) of Example 8 in Test Example 3. The horizontal axis shows the time (hour) and the vertical axis shows the concentration of timolol in iris and ciliary body ($\mu g/g$). Each value shows the mean value±standard deviation (5 samples). The black circles and the black squares show each case that the eye drop of Example 8 or the eye drop of Example 8 without sorbic acid is instilled, respectively. ** shows the significance $p<0.01$ and * shows $p<0.05$, against the control group by the student-t test.

(3) The drug concentration-time profiles of timolol in iris-ciliary body is shown in FIG. 7. The concentration of timolol in iris-ciliary body at each post-instillation times of 15 minutes and 30 minutes for the eye drop containing sorbic acid was about 3.1 times higher and about 3.4 times higher, respectively, than that of the control. Also, similarly with the drug concentrations in aqueous humor and cornea, the concentration of timolol in iris-ciliary body was higher at every time and the area under the curve (AUC) for the drug concentration-time profiles in iris-ciliary body was about 2.1 times higher for the eye drop containing sorbic acid than that of the control.

The above results show that the penetration of timolol maleate into aqueous humor, cornea and iris-ciliary body is promoted immediately after the instillation by incorporating sorbic acid in the eye drop containing timolol maleate. It is also shown that the retention of timolol maleate in the ocular tissues is improved because the concentration of timolol maleate in the ocular tissues kept at the higher concentration level at each time than that of 0.5% Timoptol® (produced by Banyu Pharmaceutical Co., Ltd.) used as the control.

TEST EXAMPLE 4

Effect of the Saturated or Unsaturated Fatty Acid on the Penetration of Carteolol Hydrochloride (Experimental Method)

50 µl of each eye drop of Example 2 (containing sorbic acid as an unsaturated fatty acid), Example 17 (containing caproic acid as a saturated fatty acid), Example 18 (containing crotonic acid as an unsaturated fatty acid) and Example 19 (containing butyric acid as a saturated fatty acid) was instilled once to each male arbino rabbit. Each rabbit was slaughtered to withdraw aqueous humor at post-instillation time of 1 hour, then the concentration of carteolol hydrochloride in aqueous humor was measured. As the control, an eye drop prepared by omitting sorbic acid from the components of Example 2 was instilled to the rabbit. In the same manner as above, the concentration of carteolol hydrochloride in aqueous humor was measured.

(Results of the Experiment)

Figure 8:
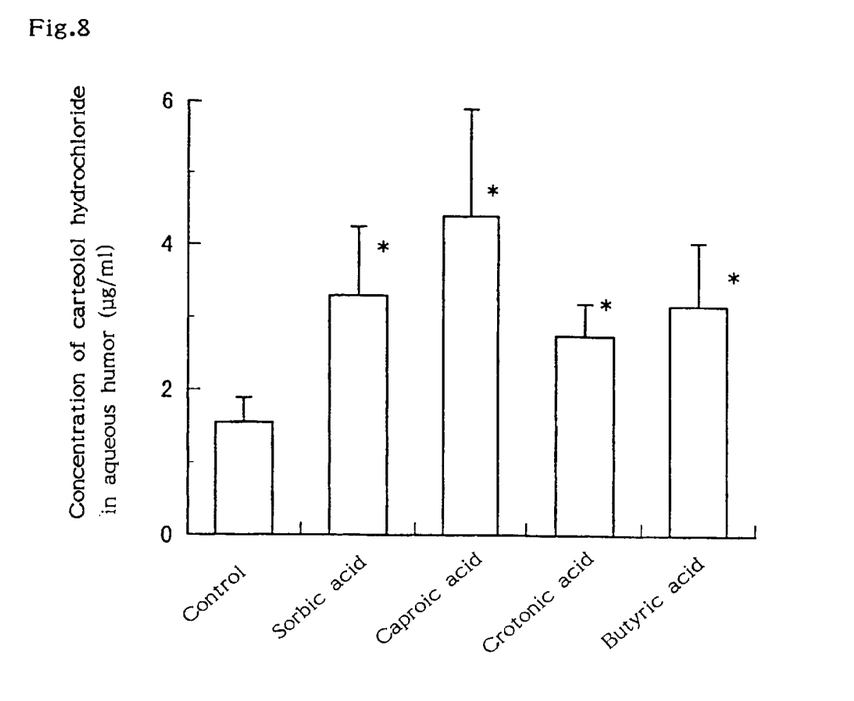
FIG. 8 is a graph showing the amount of carteolol hydrochloride penetrated in aqueous humor at the time of 1 hour after the instillation of the eye drop (containing 2 w/v % carteolol hydrochloride) of Examples 2, 17, 18 and 19 in Test Example 4. The horizontal axis shows the test group and the vertical axis shows the concentration of carteolol hydrochloride in aqueous humor ($\mu g/ml$). Each value shows the mean value±standard deviation (3 samples). * shows the significance $p<0.05$ against the control group by the student-t test.

The results are shown in FIG. 8. The concentration of cartolol hydrochloride in aqueous humor at post-instillation time of 1 hour was about 2.1 times higher for the eye drop containing sorbic acid, about 2.8 times higher for the eye drop containing caproic acid, about 1.8 time higher for the eye drop containing crotoic acid and about 2 times higher for the eye drop containing butyric acid respectively than that of the control without the fatty acid.

The above results show that the penetration of carteolol hydrochloride into the eye is promoted by incorporating the saturated or unsaturated fatty acid in the eye drop containing carteolol hydrochloride.

TEST EXAMPLE 5

Effect of Sorbic Acid on the Penetration of Betaxolol Hydrochloride (Experimental Method)

50 µl of each eye drop of Example 13 (betaxolol hydrochloride:sorbic acid=1:2, mole ratio) and Example 14 (betaxolol hydrochloride:sorbic acid=1:5, mole ratio) was instilled to each male arbino rabbit, respectively. Each rabbit was slaughtered to withdraw aqueous humor at post-instillation time of 1 hour, then the concentration of betaxolol hydrochloride in aqueous humor was measured. As the control, an eye drop prepared by omitting sorbic acid in Example 13 was instilled to the rabbit in the same manner as above, the concentration of betaxolol hydrochloride in aqueous humor was measured.

(Results of the Experiment)

The concentration of betaxolol hydrochloride in aqueous humor at post-instillation time of 1 hour was 2.57±1.45 µg/ml (3 samples) for the eye drop of Example 13 and 2.89±0.75 µg/ml (4 samples) for the eye drop of Example 14, were about 2.2 times higher and about 2.5 times higher, respectively than 1.16±0.45 µg/ml (4 samples) for the eye drop without sorbic acid used as the control. The results show that the penetration of betaxolol hydrochloride into the eye is promoted by incorporating sorbic acid in the eye drop containing betaxolol hydrochloride.

INDUSTRIAL APPLICABILITY

Because the eye drop of the present invention promotes the penetration of the β-blocker into the eye and improves the retention of the β-blocker in the ocular tissues, the times of the instillation can be reduced and the apprehension concerning the frequent instillations can be avoided and therefore, it is useful for the eye drop. Also, it is useful for eye drop giving the sufficient effect for lowering the intraocular pressure even when the content of the β-blocker is reduced.

The present invention is based on Japanese Patent Applications No. 9/302802 and No. 10/250009, and contains the whole contents thereof in the present specification.

What is claimed is:

1. An eye drop comprising 0.1 to 2 w/v % of a drug selected from the group consisting of carteolol, timolol betaxolol and a salt thereof, and 0.04 to 2 w/v % of a sorbic acid or a salt thereof, wherein the eye drop promotes penetration of the drug into an eye and improves retention time of the drug in ocular tissues by incorporation of sorbic acid or salt thereof.

2. An eye drop comprising carteolol or a salt thereof and sorbic acid or a salt thereof, wherein the ratio of sorbic acid or a salt thereof to carteolol or a salt thereof is 0.2 to 5 part by mole of the former to 1 part by mole of the latter, and wherein the eye drop promotes penetration of carteolol or a salt thereof into an eye and improves retention time of carteolol or a salt thereof in ocular tissues.

3. An eye drop comprising timolol or a salt thereof and sorbic acid or a salt thereof, wherein the ratio of sorbic acid or a salt thereof to timolol or a salt thereof is 0.2 to 10 part by mole of the former to 1 part by mole of the latter, and wherein the eye drop promotes penetration of timolol or a salt thereof into an eye and improves retention time of timolol or a salt thereof in ocular tissues.

4. An eye drop comprising betaxolol or a salt thereof and sorbic acid or a salt thereof wherein the ratio of sorbic acid or a salt thereof to betaxolol or a salt thereof is 0.5 to 10 part by mole of the former to 1 part by mole of the latter, and wherein the eye drop promotes penetration of betaxolol or a salt thereof into an eye and improves retention time of betaxolol or a salt thereof in ocular tissues.

* * * * *